(12) United States Patent
Murphy-Chutorian et al.

(10) Patent No.: US 12,186,466 B2
(45) Date of Patent: Jan. 7, 2025

(54) TRANSFER CATHETER FOR ULTRAVIOLET DISINFECTION

(71) Applicant: PuraCath Medical, Inc., San Francisco, CA (US)

(72) Inventors: Douglas Murphy-Chutorian, Palo Alto, CA (US); James R. Kermode, Los Altos, CA (US); Justin A. Lance, Hollister, CA (US); Julia A. Rasooly, San Francisco, CA (US); Michael Rasooly, San Francisco, CA (US); Charles Martin Schwimmer, San Jose, CA (US)

(73) Assignee: PuraCath Medical, Inc., San Francisco, CA (US)

( * ) Notice: Subject to any disclaimer, the term of this patent is extended or adjusted under 35 U.S.C. 154(b) by 869 days.

(21) Appl. No.: 17/314,862

(22) Filed: May 7, 2021

(65) Prior Publication Data
US 2021/0322753 A1    Oct. 21, 2021

Related U.S. Application Data

(62) Division of application No. 14/731,110, filed on Jun. 4, 2015, now Pat. No. 11,007,361.
(Continued)

(51) Int. Cl.
*A61M 39/22*    (2006.01)
*A61L 2/10*    (2006.01)
(Continued)

(52) U.S. Cl.
CPC .............. *A61M 1/285* (2013.01); *A61L 2/10* (2013.01); *A61M 1/168* (2013.01); *A61M 1/287* (2013.01); *A61M 1/288* (2014.02); *A61M 1/3643* (2013.01); *A61M 1/3644* (2014.02); *A61M 1/3649* (2014.02); *A61M 39/00* (2013.01); *A61M 39/20* (2013.01); *A61M 39/22* (2013.01); *A61M 39/225* (2013.01); *A61M 39/24* (2013.01); *A61L 9/18* (2013.01); *A61L 2202/24* (2013.01); *A61M 2025/0019* (2013.01); *A61M 2039/0018* (2013.01); *A61M 2039/2453* (2013.01); *A61M 2209/10* (2013.01)

(58) Field of Classification Search
CPC .... A61M 1/285; A61M 1/168; A61M 39/225; A61L 2/10; A61L 2202/24
See application file for complete search history.

(56) References Cited

U.S. PATENT DOCUMENTS 3,517,669 A    6/1970    Buono et al.
3,572,375 A    3/1971    David
(Continued)

*Primary Examiner* — Sean E Conley
(74) *Attorney, Agent, or Firm* — Vorys, Sater, Seymour and Pease LLP; Khaled Shami

(57) ABSTRACT

Disclosed herein are devices and methods related to UV disinfection of a transfer catheter during peritoneal dialysis. The transfer catheter comprises a first and second end, the second end comprising a transfer valve. The transfer valve body comprises an inlet, outlet, and a flush hole. The valve core comprises a notch configured to allow fluid flow between the various flow paths. The valve core and body are positioned off axis with respect to the fluid flow path. The transfer catheter can allow for a small volume kill zone, which can minimize the amount of UV required to disinfect the catheter.

22 Claims, 18 Drawing Sheets

Related U.S. Application Data

(60) Provisional application No. 62/008,433, filed on Jun. 5, 2014.

(51) Int. Cl.

| | | |
|---|---|---|
| *A61M 1/16* | (2006.01) | |
| *A61M 1/28* | (2006.01) | |
| *A61M 1/36* | (2006.01) | |
| *A61M 39/00* | (2006.01) | |
| *A61M 39/20* | (2006.01) | |
| *A61M 39/24* | (2006.01) | |
| *A61L 9/18* | (2006.01) | |
| *A61M 25/00* | (2006.01) | |

(56) References Cited

U.S. PATENT DOCUMENTS

| | | | |
|---|---|---|---|
| 3,626,938 A | 12/1971 | Versaci | |
| 3,986,508 A | 10/1976 | Barrington | |
| 4,146,055 A | 3/1979 | Ryder et al. | |
| 4,209,013 A | 6/1980 | Alexander et al. | |
| 4,232,428 A | 11/1980 | Johansson | |
| 4,242,310 A | 12/1980 | Greff et al. | |
| 4,256,135 A | 3/1981 | Hannah | |
| 4,336,223 A | 6/1982 | Hillman | |
| 4,340,052 A | 7/1982 | Michael et al. | |
| 4,346,704 A | 8/1982 | Kulle | |
| 4,412,834 A | 11/1983 | Kulin et al. | |
| 4,433,244 A | 2/1984 | Hogan | |
| 4,439,188 A | 3/1984 | Michael et al. | |
| 4,440,207 A | 4/1984 | Genatempo et al. | |
| 4,457,794 A | 7/1984 | Kotera et al. | |
| 4,469,835 A | 9/1984 | Laurin | |
| 4,473,369 A | 9/1984 | Lueders et al. | |
| 4,475,900 A | 10/1984 | Popovich et al. | |
| 4,500,788 A | 2/1985 | Kulin et al. | |
| 4,541,829 A | 9/1985 | Munsch et al. | |
| 4,573,980 A | 3/1986 | Karrasch et al. | |
| 4,608,472 A | 8/1986 | Kato | |
| 4,655,762 A | 4/1987 | Rogers | |
| 4,745,950 A | 5/1988 | Mathieu | |
| 4,774,415 A | 9/1988 | Biegel et al. | |
| 4,877,964 A | 10/1989 | Tanaka et al. | |
| 4,878,516 A | 11/1989 | Mathieu | |
| 4,882,496 A | 11/1989 | Bellotti et al. | |
| 4,948,980 A | 8/1990 | Wedekamp | |
| 4,949,723 A | 8/1990 | Dean et al. | |
| 4,950,230 A | 8/1990 | Kendell | |
| 4,950,260 A | 8/1990 | Bonaldo | |
| 4,980,374 A | 12/1990 | Steudle et al. | |
| 5,047,011 A | 9/1991 | Caron et al. | |
| 5,053,003 A * | 10/1991 | Dadson | A61M 1/28 |
| | | | 604/28 |
| 5,057,074 A | 10/1991 | Suzuki et al. | |
| 5,105,853 A | 4/1992 | Lie | |
| 5,147,321 A | 9/1992 | Slonina et al. | |
| 5,190,534 A | 3/1993 | Kendell | |
| 5,221,267 A | 6/1993 | Folden | |
| 5,242,150 A | 9/1993 | Shiffler et al. | |
| 5,336,173 A | 8/1994 | Folden | |
| 5,417,673 A | 5/1995 | Gordon | |
| 5,427,135 A | 6/1995 | Kieper | |
| 5,439,451 A | 8/1995 | Collinson et al. | |
| 5,536,258 A | 7/1996 | Folden | |
| 5,540,668 A | 7/1996 | Wilson, Jr. et al. | |
| 5,555,908 A | 9/1996 | Edwards et al. | |
| 5,603,902 A | 2/1997 | Maltais et al. | |
| 5,612,001 A | 3/1997 | Matschke | |
| 5,640,690 A | 6/1997 | Kudma | |
| 5,713,850 A | 2/1998 | Heilmann et al. | |
| 5,714,119 A | 2/1998 | Kawagoe et al. | |
| 5,832,959 A | 11/1998 | Szymczakowski et al. | |
| 5,855,203 A | 1/1999 | Matter | |
| 6,027,489 A | 2/2000 | Galato | |
| 6,120,166 A | 9/2000 | Price | |
| 6,228,332 B1 | 5/2001 | Dunn et al. | |
| 6,245,570 B1 | 6/2001 | Grimm et al. | |
| 6,418,257 B1 | 7/2002 | Nath | |
| 6,461,568 B1 | 10/2002 | Eckhardt | |
| 6,461,569 B1 | 10/2002 | Boudreaux | |
| 6,470,888 B1 | 10/2002 | Matter | |
| 6,485,483 B1 | 11/2002 | Fujii | |
| 6,569,564 B1 | 5/2003 | Lane | |
| 6,592,558 B2 | 7/2003 | Quah | |
| 6,682,507 B2 | 1/2004 | Irish | |
| 6,803,363 B2 | 10/2004 | Polaschegg | |
| 6,834,984 B2 | 12/2004 | Tausch et al. | |
| 7,083,605 B2 | 8/2006 | Miyahara | |
| 7,198,611 B2 | 4/2007 | Connell et al. | |
| 7,232,428 B2 | 6/2007 | Inukai et al. | |
| 7,232,429 B2 | 6/2007 | Moreci | |
| 7,274,847 B2 | 9/2007 | Gowda et al. | |
| 7,452,346 B2 | 11/2008 | Axelsson | |
| 7,497,849 B2 | 3/2009 | Fangrow, Jr. et al. | |
| 7,806,851 B2 | 10/2010 | Cerasoli | |
| 7,955,295 B2 | 6/2011 | Lee et al. | |
| 8,197,087 B2 | 6/2012 | Sobue et al. | |
| 8,282,829 B2 | 10/2012 | Yu et al. | |
| 8,431,074 B2 | 4/2013 | Neer | |
| 8,478,385 B2 | 7/2013 | Liu et al. | |
| 8,585,681 B2 | 11/2013 | Boenig et al. | |
| 8,641,659 B2 | 2/2014 | Soykan et al. | |
| 8,946,653 B2 | 2/2015 | Victor et al. | |
| 2002/0177772 A1* | 11/2002 | Altman | B82Y 5/00 |
| | | | 600/431 |
| 2003/0010927 A1 | 1/2003 | Wedekamp | |
| 2003/0017073 A1 | 1/2003 | Eckhardt et al. | |
| 2004/0195538 A1 | 10/2004 | Raines et al. | |
| 2005/0013729 A1 | 1/2005 | Brown-Skrobot et al. | |
| 2005/0124970 A1 | 6/2005 | Kunin et al. | |
| 2005/0163655 A1 | 7/2005 | Lin et al. | |
| 2005/0258762 A1 | 11/2005 | Beland et al. | |
| 2005/0261621 A1 | 11/2005 | Perez | |
| 2006/0027270 A1 | 2/2006 | Truitt et al. | |
| 2006/0122559 A1 | 6/2006 | Shia et al. | |
| 2006/0147339 A1 | 7/2006 | Hunter et al. | |
| 2006/0163515 A1 | 7/2006 | Ruschke et al. | |
| 2006/0186010 A1 | 8/2006 | Warnack et al. | |
| 2007/0023710 A1 | 2/2007 | Tom et al. | |
| 2007/0176117 A1 | 8/2007 | Redmond et al. | |
| 2007/0179473 A1 | 8/2007 | Masters et al. | |
| 2007/0232989 A1 | 10/2007 | Kitani et al. | |
| 2007/0274879 A1 | 11/2007 | Millikin | |
| 2007/0287953 A1 | 12/2007 | Ziv et al. | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |
| 2008/0195031 A1 | 8/2008 | Kitani et al. | |
| 2008/0306454 A1 | 12/2008 | Sikora | |
| 2009/0012451 A1 | 1/2009 | Sobue et al. | |
| 2009/0149776 A1 | 6/2009 | Adams | |
| 2009/0182309 A1 | 7/2009 | Muffly | |
| 2009/0205664 A1 | 8/2009 | Lyon | |
| 2009/0257910 A1 | 10/2009 | Segal | |
| 2009/0259203 A1 | 10/2009 | Hu et al. | |
| 2009/0289015 A1 | 11/2009 | Levy | |
| 2009/0320316 A1 | 12/2009 | Zakai | |
| 2010/0072399 A1 | 3/2010 | Street et al. | |
| 2010/0072506 A1 | 3/2010 | Bae et al. | |
| 2010/0249586 A1 | 9/2010 | Cocker et al. | |
| 2010/0249747 A1* | 9/2010 | Mills | A61K 45/06 |
| | | | 514/56 |
| 2011/0028915 A1 | 2/2011 | Siopes et al. | |
| 2011/0064608 A1 | 3/2011 | Lee et al. | |
| 2011/0085936 A1 | 4/2011 | Haytman et al. | |
| 2011/0165020 A1 | 7/2011 | Tryggvason et al. | |
| 2011/0213339 A1 | 9/2011 | Bak | |
| 2011/0224624 A1 | 9/2011 | Geller | |
| 2012/0053512 A1 | 3/2012 | Muse et al. | |
| 2012/0161032 A1 | 6/2012 | Arcand et al. | |
| 2012/0205825 A1 | 8/2012 | Nagafuji et al. | |
| 2012/0206992 A1 | 8/2012 | Stewart | |
| 2012/0296151 A1 | 11/2012 | Curtis et al. | |

(56) References Cited

U.S. PATENT DOCUMENTS

| | | |
|---|---|---|
| 2012/0310179 A1 | 12/2012 | Truitt et al. |
| 2012/0321509 A1 | 12/2012 | Bak |
| 2013/0131626 A1 | 5/2013 | Thompson et al. |
| 2013/0204227 A1 | 8/2013 | Bochenko et al. |
| 2013/0303996 A1 | 11/2013 | Rasooly et al. |
| 2013/0323119 A1 | 12/2013 | Alwan |
| 2014/0076454 A1 | 3/2014 | Kjar et al. |
| 2014/0205498 A1 | 7/2014 | Bak et al. |
| 2014/0276215 A1 | 9/2014 | Nelson et al. |
| 2014/0276345 A1 | 9/2014 | Silin et al. |
| 2014/0334974 A1 | 11/2014 | Rasooly et al. |
| 2015/0258230 A1 | 9/2015 | Victor et al. |

\* cited by examiner

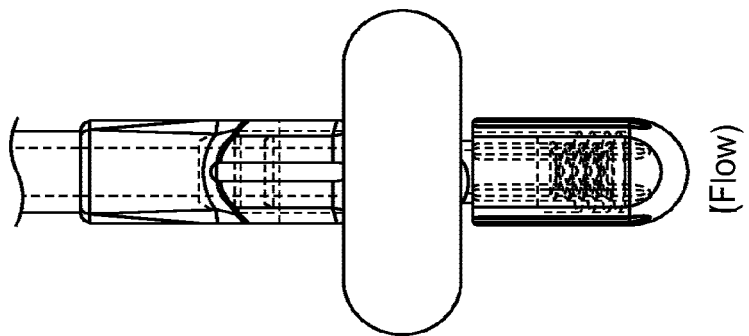
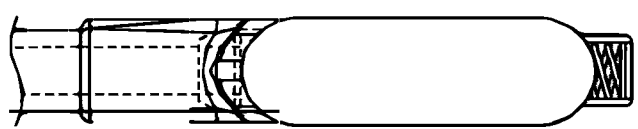
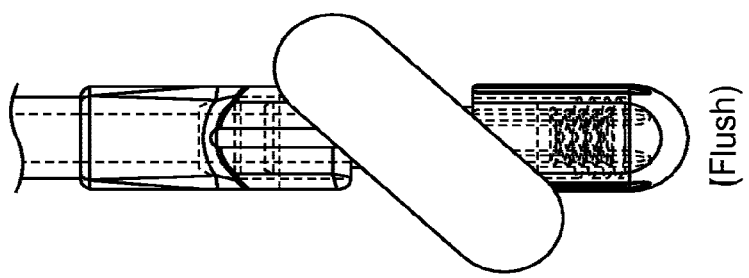

US 12,186,466 B2

TRANSFER CATHETER FOR ULTRAVIOLET DISINFECTION

CROSS REFERENCE TO RELATED APPLICATIONS

This application is a division of U.S. patent application Ser. No. 14/731,110, filed Jun. 4, 2015 and claims the benefit of U.S. Provisional Patent Application No. 62/008,433, filed Jun. 5, 2014.

INCORPORATION BY REFERENCE

All publications and patent applications mentioned in this specification are herein incorporated by reference to the same extent as if each individual publication or patent application was specifically and individually indicated to be incorporated by reference.

FIELD

This application relates generally to sterilization of connectors, more particularly connectors used in a medical application, for example during peritoneal dialysis (PD).

BACKGROUND

Peritoneal dialysis can be used as a treatment for patients with severe chronic kidney disease. Fluid is introduced through a tube in the abdomen and flushed out periodically either while the patients sleeps, in automated peritoneal dialysis or during regular dialysis sessions through the day, as in continuous ambulatory peritoneal dialysis.

As shown in FIG. 1, a patient undergoing peritoneal dialysis can have an indwelling catheter surgically inserted into the abdomen. A transfer catheter 2 can be attached to the indwelling catheter 4. The transfer catheter can be replaced, in a sterile environment, such as at a clinic, every few months to a year. Between dialysis sessions, the patient wears the transfer catheter against the body. During dialysis sessions, the transfer catheter can be connected to a drain bag to drain fluid present in the abdomen and a fresh dialysate bag to introduce fluid to the abdomen. The drain bag and dialysate bags can be attached in series or can be attached in parallel, using a Y-shaped solution set catheter 6. Prior to each treatment, the patient connects the tip of the transfer catheter to new dialysis tubing using rigorous aseptic techniques to maintain sterility. The same sterile technique must be employed when disconnecting the catheters as well. Once the patient feels confident enough to perform the procedure at home, and after many months of practice, the time to connect and start PD takes 20-30 minutes. The patient and anyone around them must always wear a mask, close doors and windows, turn off fans, and thoroughly wash hands for 2 minutes prior to connecting or disconnecting catheters. If sterility is compromised at any time, the component being used must be replaced and the whole process started again.

This is obviously a complicated and time-consuming process that is highly reliant on patient compliance. If a patient fails to adhere to any of the strict steps of the sterilization procedure, he or she faces a greatly increased risk of a serious infection, commonly referred to as peritonitis. This type of internal infection, if not caught early, may lead to sepsis and death of the patient. Typically, peritoneal dialysis (PD) patients experience a 50% chance of infection during the first 12 to 18 months and experience 15% mortality/yr directly related to the infection. In addition to seriously endangering a patient's health, infections in peritoneal dialysis are also very costly to treat. The average total charges from a peritonitis hospital stay are roughly $50,000 dollars and the entire annual cost on the healthcare system is around $1.5 billion. Given that the noncompliance rate for a standard peritoneal dialysis procedure is around 30%, there is a huge need to help reduce the health and financial burdens of infection.

Ultraviolet (UV) disinfection systems are known in the art. U.S. Pat. Nos. 4,882,496; 7,834,328; 4,620,845; 6,461,568 and U.S. Publication Nos. 2005/0013729 and 2007/0274879, the disclosures of which are incorporated by reference herein in their entireties, describe such systems. However, such systems can be cumbersome, making them difficult for a user to use. Additionally, such systems tend to rely on UV disinfection for complete disinfection, which can, in the absence of proper components and connectors, limit the effectiveness of the disinfection.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 12A-D illustrate an embodiment of a method of using the transfer catheter.

DETAILED DESCRIPTION

Embodiments of the transfer catheter disclosed herein can be used by peritoneal dialysis (PD) patients. The transfer catheter can be attached to the patient's indwelling catheter 4. The transfer catheter can comprise a valve at the end away from the patient's indwelling catheter. During a peritoneal dialysis session, the patient can connect the transfer catheter to the solution set catheter(s). The patient can use the valve on the transfer catheter to flush away any residual fluid within the valve or fluid which may be sequestered by a non UV-transmissive solution set catheter. The connection between the transfer catheter and the solution set catheter, including the valve, can then be sterilized through exposure to UV light. It has been found that flushing the catheter line in combination with UV sterilization can provide more effective disinfection than UV sterilization alone. Features of the transfer catheter, as will be disclosed in more detail hereinafter, can allow for a minimal volume of fluid to be disinfected or exposed to UV light. Minimizing the volume needed to be disinfected allows for the transfer catheter and valve to comprise a small volume kill zone, and can allow for the transfer catheter and valve to comprise a small size and low profile, which can increase patient comfort while wearing the transfer catheter, for example, between dialysis sessions. Additionally, minimizing the volume to be disinfected can allow for less UV light required for disinfection, which can allow for smaller/fewer UV bulbs and power sources, which in turn, can allow for a smaller UV light applicator. Minimizing the size of the UV applicator can increase patient comfort and convenience.

Figure 1:
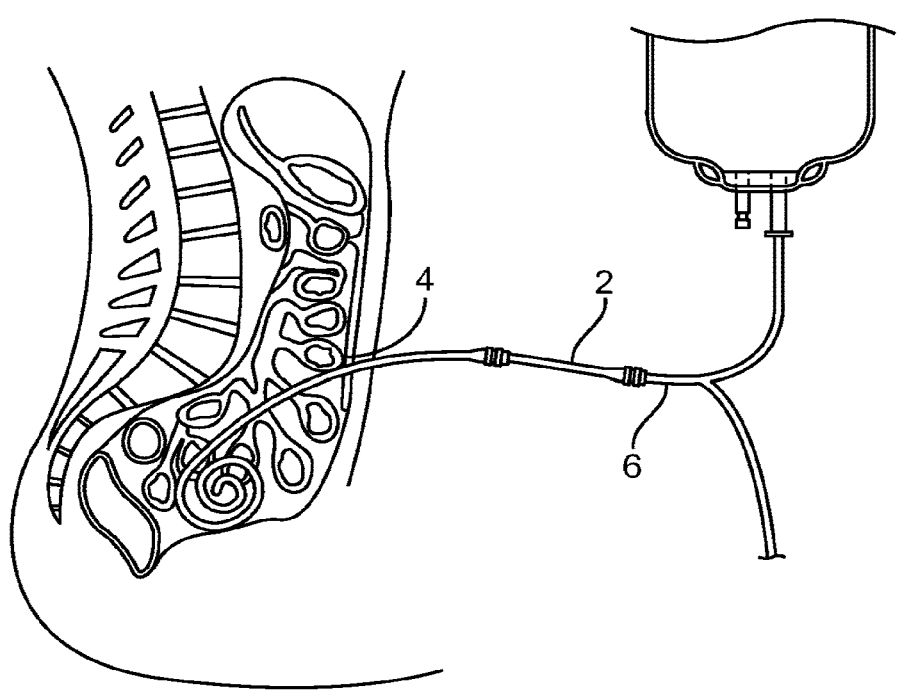
FIG. 1 is an illustration of a conventional peritoneal dialysis setup.
Figure 2:
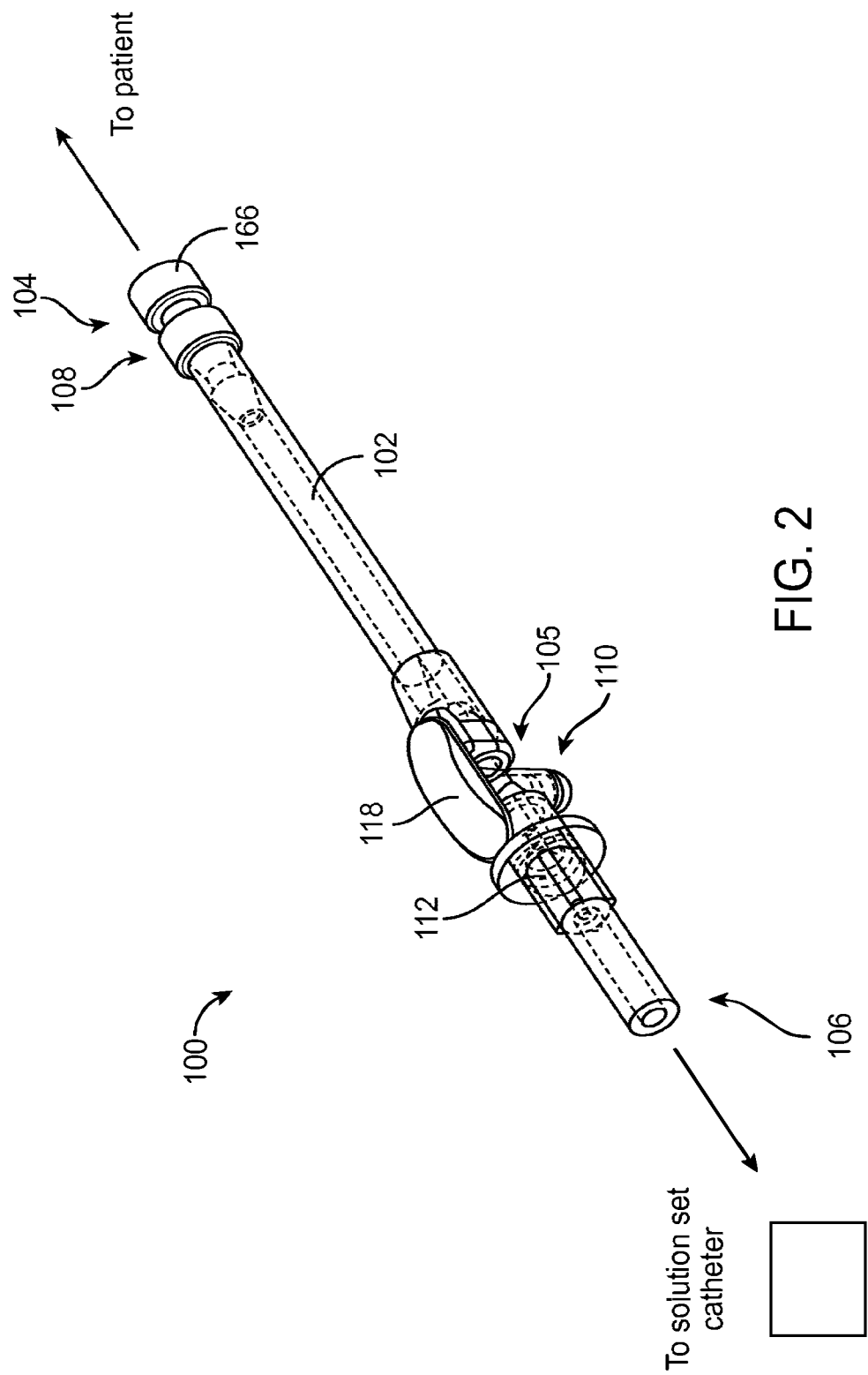
FIG. 2 is an illustration of an embodiment of a transfer catheter.

FIG. 2 illustrates an embodiment of a transfer catheter 100 that can be used like the transfer catheter 2 of FIG. 1. The transfer catheter comprises a tubular body 102, a first end 104, and a second end 106. The transfer catheter 100 comprises a first connector 108 positioned at or near the first end 104, and a transfer valve 110 positioned at or near the second end 106. The transfer catheter 100 is shown disconnected from the indwelling catheter, and has a cap 166 at the first end.

The transfer valve 110 is connected to the tubular body 102 at a first end via a first connector 105 and has a second connector 112 at its second end. The first connector 105 can be for example, a barb connection, as best seen in FIG. 9B. Other connections are also possible. The second connector 112 can be a Luer fitting. The second connector 112 can comprise threads (e.g., ISO standard, full height, partial diameter threads). A Luer fitting can help ensure compatibility of the transfer catheter 100 with connectors from other systems. Other connectors are also possible (e.g., barb swagelock, slip, etc.).

Figure 3:
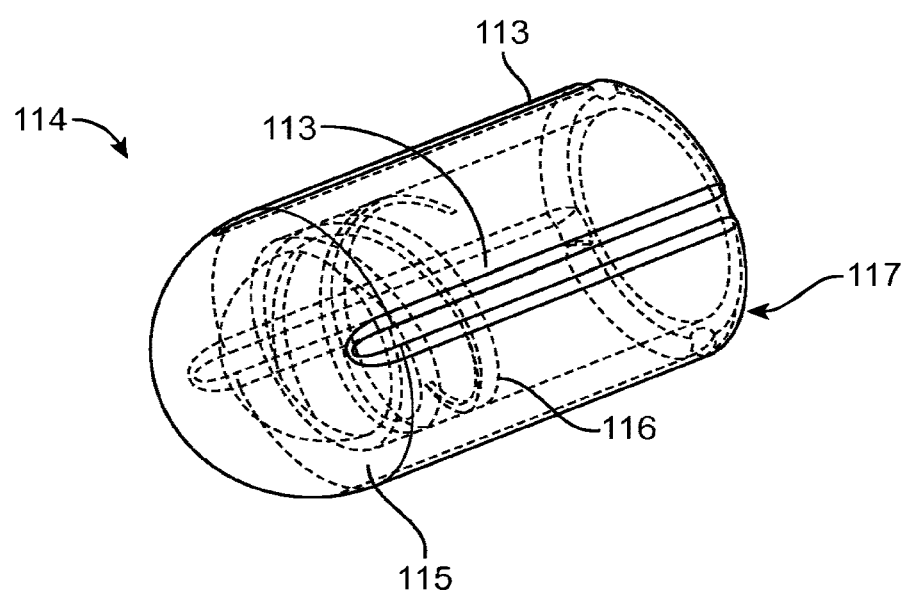
FIG. 3 is an illustration of an embodiment of a cover.

Referring now to FIG. 3, the connector 112 may include a cover 114. The cover can be configured to mate with the connector 112. For example, the cover 114 can comprise threads 115 configured to mate with threads 111 (shown in FIG. 4A) on the connector 112, as shown in FIG. 3. The threads can comprise ISO Standard thread pitch (e.g., double-start thread pitch). In some embodiments, at least a portion of the threads (e.g., portion 116) comprise a shallower (e.g., shallower than standard thread depth, shallower than the connector 112 thread depth) thread depth. The cover 114 comprising a shallower thread depth can help ensure that the cover 114 strips before stripping the mating part (e.g., the connector 112) when the cover 114 is over torqued. The cover 114 can comprise grooves 113 which can be used to aid grip in attaching and removing the cover.

The cover 114 can be configured to be UV transparent (e.g., UV-C transparent). UV transparency can allow components underlying the cover 114 (e.g., the connector 112) to be distributed non-sterile and subsequently disinfected by the user. In some embodiments, the cover 114 comprises a UV-transparent material (e.g., cyclic olefin copolymer (COC) (e.g., Topas®)). Other materials are also possible (e.g., Mitsui chemicals TPX). The cover 114 can comprise a smooth outer surface, which can discourage over-torqueing and improve patient comfort while wearing the transfer catheter. The cover 114 can also comprise a smooth end (e.g., hemispherically shaped). This shape can allow the cover 114 to be comfortable to wear against a patient's skin.

Figure 4A:
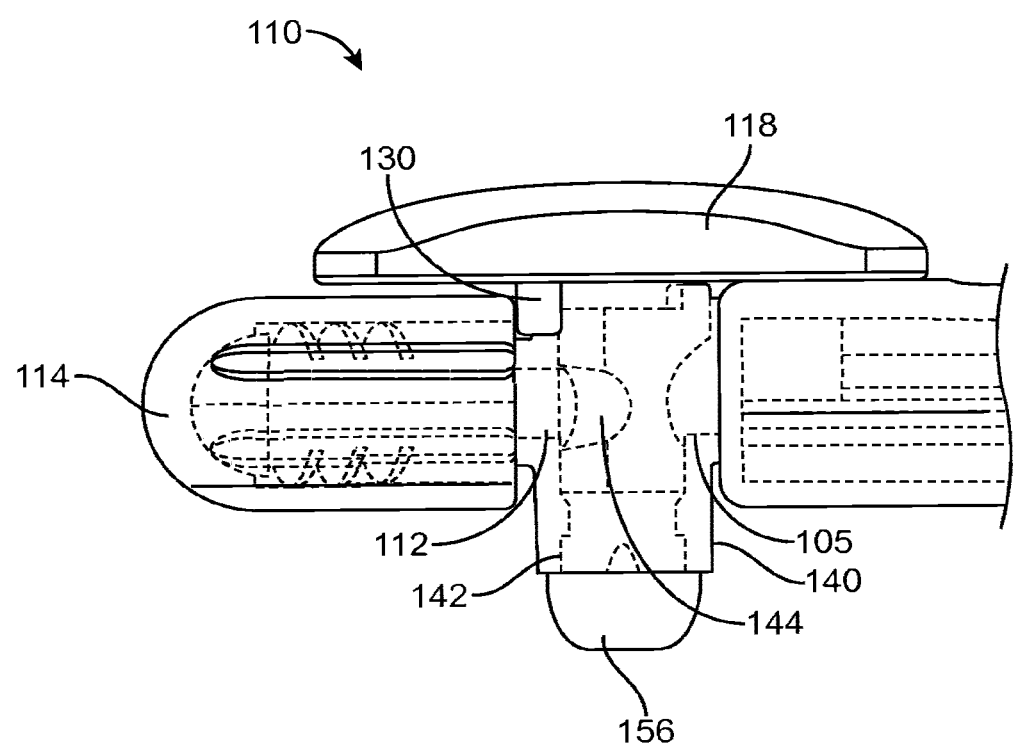
FIG. 4A is an illustration of a side view of an embodiment of a transfer valve including the valve handle.
Figure 4B:
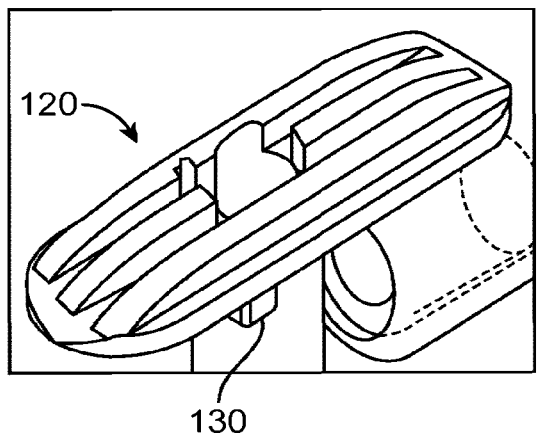
FIGS. 4B-4D are illustrations of top and bottom views of embodiments of a valve handle.
Figure 4C:
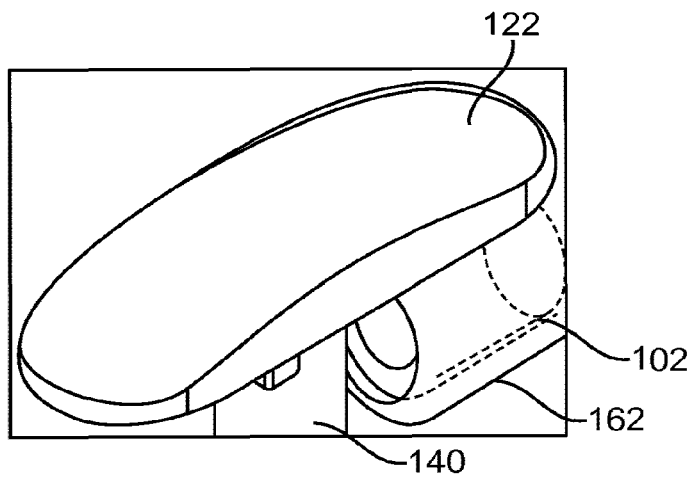
Figure 4D:
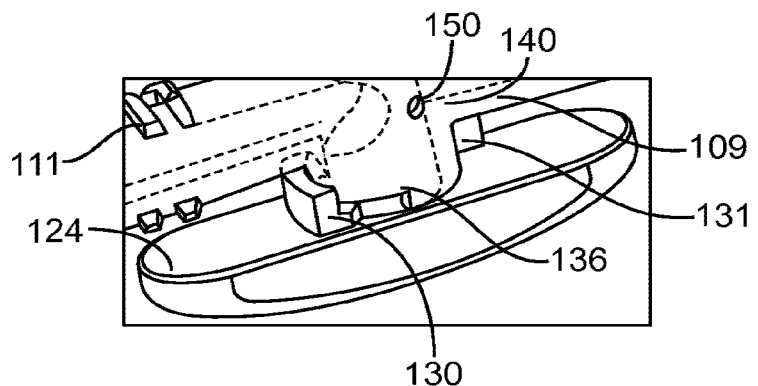
Figure 4E:
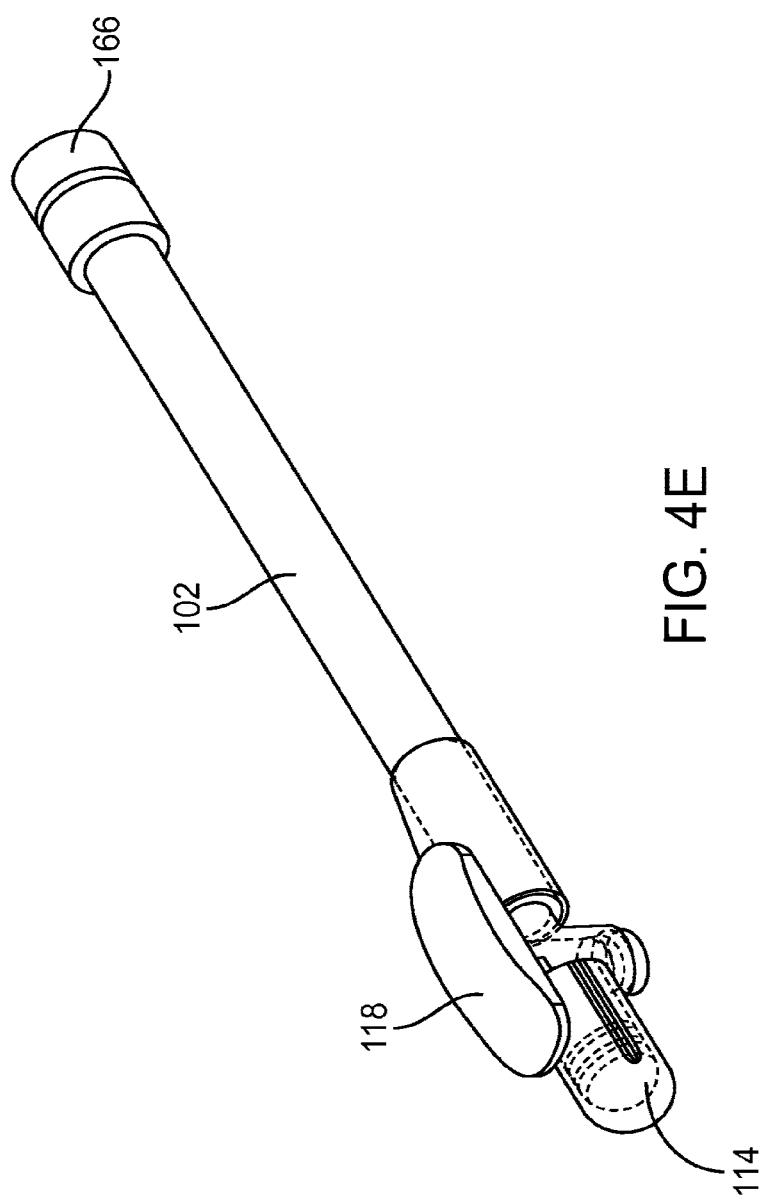
FIG. 4E is an illustration of an embodiment of a transfer catheter.
Figure 4F:
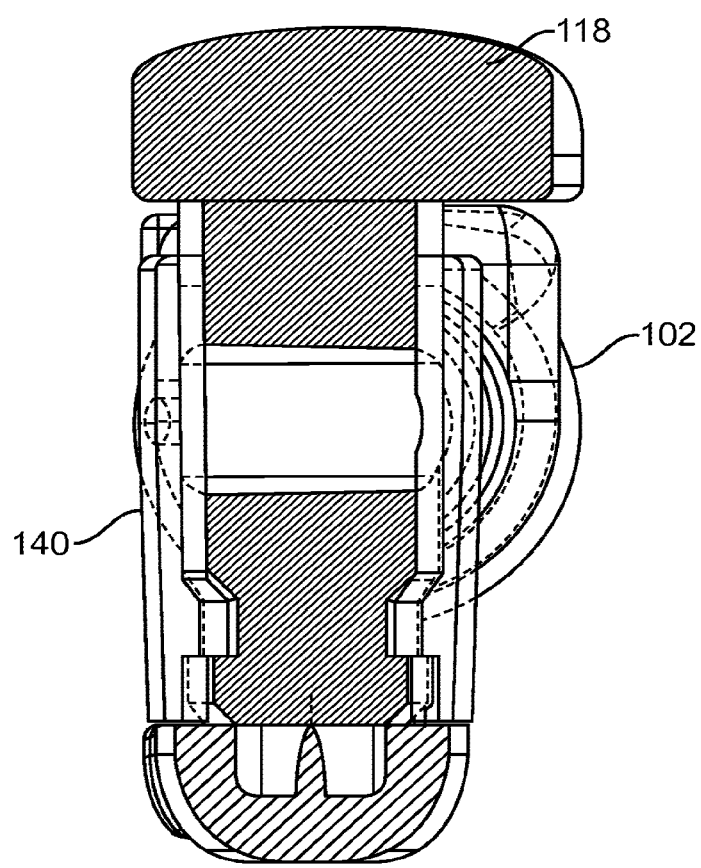
FIG. 4F is an illustration of an end view of an embodiment of a transfer catheter.
Figure 4G:
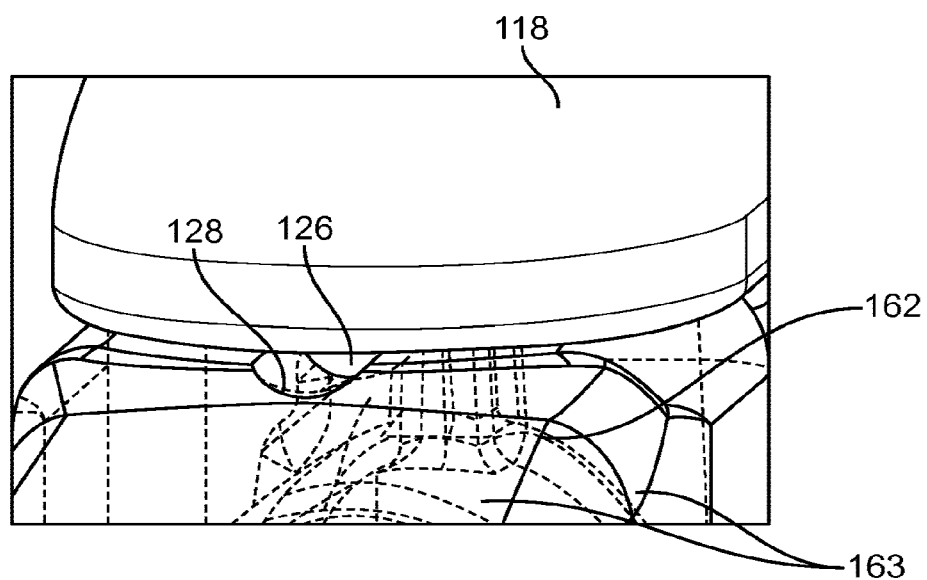
FIG. 4G is an illustration of an embodiment of a valve handle.
Figure 4H:
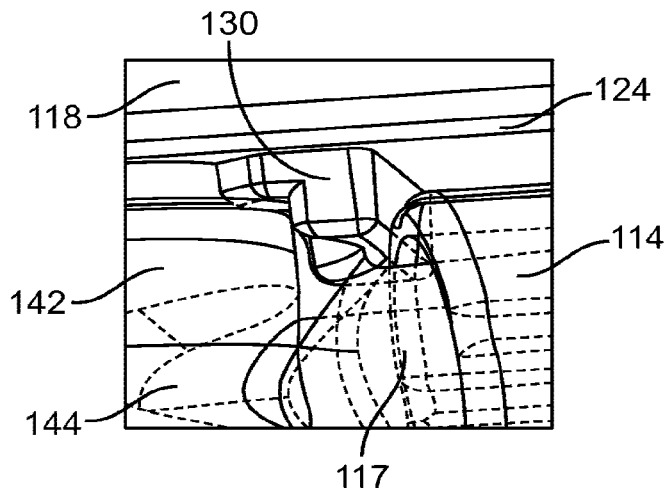
FIGS. 4H-4J are illustrations of embodiments of a valve rib.
Figure 4I:
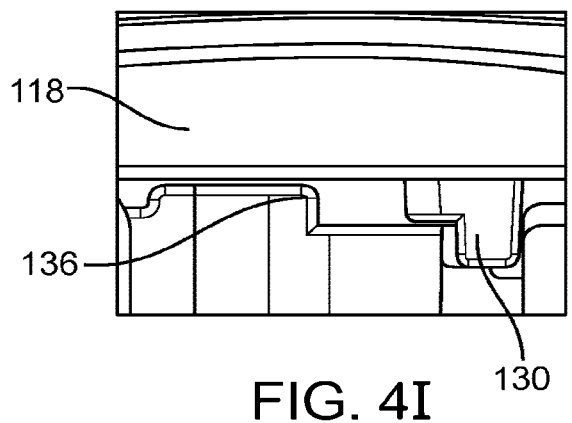
Figure 4J:
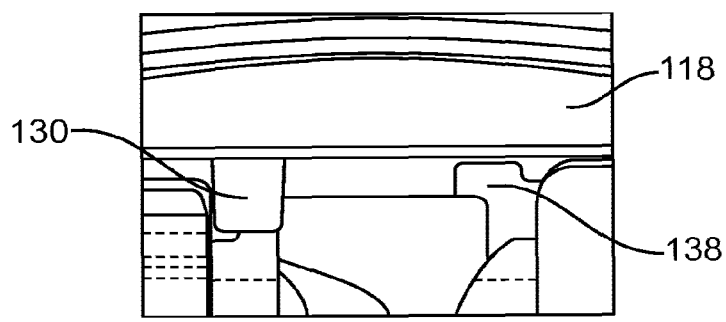

Moving to FIG. 4A, the length and diameter of the cover can be selected to interact with the transfer valve 110. For example, the length and/or diameter of the cover can be selected to allow the cover to act as a handle lock to prevent the transfer valve 110 from rotating. The cover can be sized and shaped to interact with a feature 130 on the valve handle 118 and prevent the valve handle from rotating, as shown in FIGS. 4H-J. The cover 114 can fit close beneath the handle 118, as shown in FIGS. 4A-C, H-J and 6, so the bottom surface 117 of the cover prevents the transfer valve 110 from rotating from the closed position. In this manner, while a patient is wearing the transfer catheter between dialysis sessions, the cover can help ensure the valve 110 stays in a closed position, maintaining the cleanliness of portions of the transfer catheter 100. Other locking mechanisms are also possible.

As mentioned above, the transfer valve 110 comprises a handle 118. The handle can comprise an underlying rigid skeleton 120 (e.g., a rigid plastic skeleton), as shown in FIG. 4B, beneath a soft overmold 122 (e.g., a soft plastic overmold), as shown in FIG. 4C. This combination can allow the handle 118 to be robust, while still being comfortable to wear against the body. A skeleton 120 can permit the use of less material when manufacturing the handle 118, which can reduce cost. The skeleton 120 can also be used to adjust structure of the handle 118, for example, to optimize patient comfort. In some embodiments, the skeleton 120 can protrude through the overmold 122 to aid in grip. The soft overmold can also make the handle easier to grip, especially when the user's hands are wet. Adding texture to the overmold can also enhance ease of gripping the handle 118. The underlying skeleton 120 can have a smooth bottom 124, as shown in FIG. 4D. In some embodiments, the bottom surface 124 can include one or more rib elements (e.g., rib 130) or other features. Because the portion beneath the handle 118 can be difficult to clean, a smooth surface can help prevent accumulation of contaminants beneath the handle 118.

The handle 118 long axis can be configured to align with the tubular body 102 in the closed position, as shown in FIGS. 4A-4E. Traditionally, valve handles will not be aligned with the inlet/outlet when in a closed position, and will instead be aligned with the flow path when in a flow position. This closed position alignment can make the handle 118 comfortable to wear against the patient's body, as the handle 118 will not be protruding as far from the tubular body 102 as it would with a different alignment. The alignment can also allow for the handle 118 to be longer without affecting patient comfort. A long valve handle 118 can be easier for a user to operate. The valve handle 118 can be longer than a typical stopcock. As noted above, this increased length can provide more leverage to a user when operating the handle, and can make use more comfortable. A handle 118 with a greater surface area can also be more comfortable for a user to wear against skin than a handle 118 with a smaller protrusion against the skin.

Figure 7:
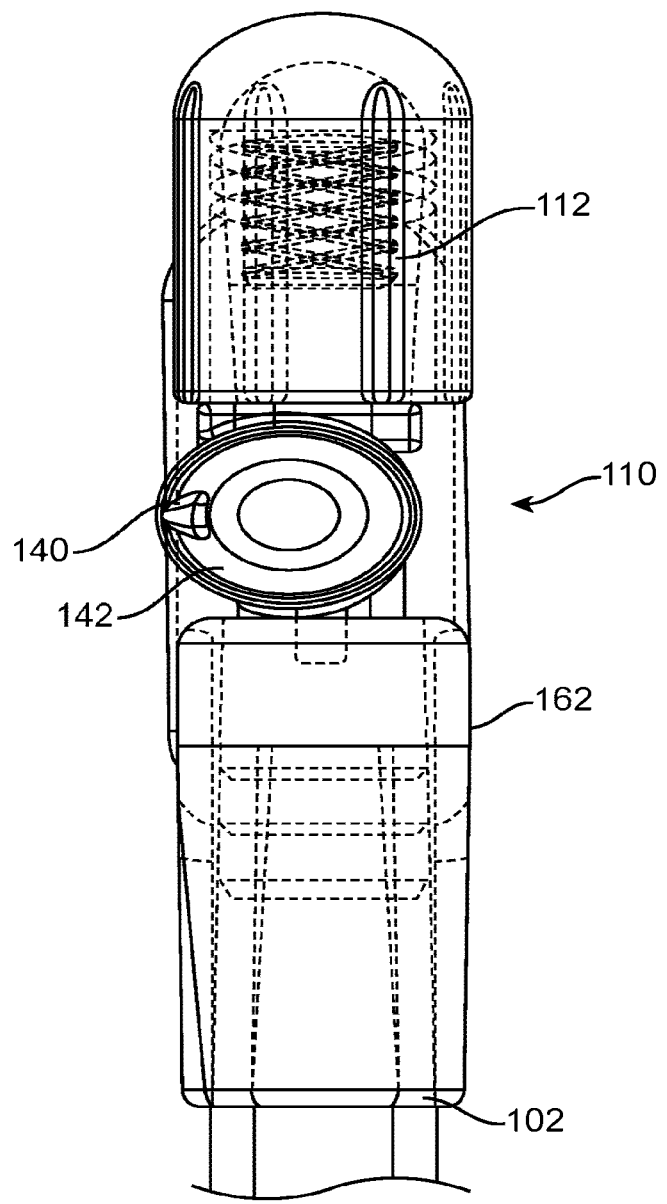
FIG. 7 is an illustration of a bottom view of an embodiment of a transfer valve.

In some embodiments, the valve core can be positioned off-axis from the tubular body 102, as described in more detail below. In such embodiments, the handle 118 can be centered on the tubular body 102 instead of the valve core, as shown in FIGS. 4F and 7. Centering the handle 118 on the tubular body 102 instead of the core can improve comfort to the user wearing the catheter 100 as such positioning minimizes protrusions poking into the user's skin.

The handle 118 can be atraumatic and ergonomic, for example, comprising an ellipsoid shape. Such a design can enhance comfort of a user wearing the handle 118 against the body. The shape of the handle 118 is also configured to blend into other components of the valve (e.g., valve core, cap, strain relief), which can help to minimize pinch points and enhance comfort.

The handle 118 can comprise a feature configured to interact with a component of the valve 110, which can serve to provide tactile user feedback of handle 118 position (e.g., closed position). The interaction can also encourage the handle 118 to stay in a closed position. For example, as shown in FIG. 4G, the handle 118 can comprise a notch 126 positioned beneath the handle configured to interface with a trough 128 on a component (e.g., strain relief) of the valve 110 beneath the handle 118.

As noted above, the handle 118 can comprise a feature configured to interact with the cover 114 to maintain the handle 118 in a particular position (e.g., a closed position). For example, as shown in FIGS. 4A-D, 4H-J and 6, the handle 118 can comprise a rib 130 on the bottom surface 124, at the front portion of the handle. The rib 130 can be generally perpendicular to the tubular body 102 axis and comprise a generally flat face. In some embodiments, the rib is at an angle other than 90° to the tubular body 102 axis. In some embodiments, the rib 130 does not have a generally flat face. The cover 114 being positioned adjacent to or abutting the rib 130 can prevent the handle 118 from rotating. This feature can be used to help maintain the valve 110 in a closed position when the cover is positioned on the catheter 100. Maintaining a closed position in the valve 110 can help ensure the cleanliness of the valve and integrity of the transfer catheter in between dialysis sessions. A closed valve position ensures no communication between any of the ports.

Moving to FIGS. 4I and 4J, the rib 130 on the handle 118 can also interface with ribs on the valve body 140 at various points along the valve rotation path. FIGS. 4I and 4J illustrate side views of the rib 130 from either side of the valve 110. For example, the rib 130 can be configured to interact with ribs 136, 138 positioned at about 45° CW and about 90° CCW from the rib 130 in the closed position. The rib 130 can prevent over-rotation of the valve 110. In some embodiments, the 45° CW position rib 136 ensures communication only between the valve flush hole 150 and the second end 106. The rib 136 or other locking feature can be positioned other than about 45° from the closed position. In some embodiments, the 90° CCW position rib 138 ensures communication only between first end and the second end. Positioning the flush hole 150 within 45° from the closed position can help allow for the flush hole 150 or the first through hole 146 to be securely sealed off in the various positions. Other interaction mechanisms are also possible (e.g., track mechanisms, etc.). Restraining valve stem movement to these positions can increase safety of the valve mechanisms. The various valve handle 118 positions are shown in more detail in FIGS. 12A-D.

The valve body 140 is positioned beneath the handle 118, as shown in FIGS. 4A, C, D, F and 10A. The valve body 140 can be generally cylindrical. The valve body 140 is in fluid communication with the first end 104 and the second end 106 of the transfer catheter 100. The valve body includes a first through hole 146 allowing fluid communication between the valve 110 and the first end 104 (not shown) through first connector 108 (e.g., a barb). The valve body 140 can be formed integrally with or attached to the first connector 108. The valve body also includes a second through hole 148 allowing fluid communication between the valve 110 and the second end 106 (not shown) through second connector 112. The valve body 140 can be formed integrally with or attached to the second connector 112. The through holes 146, 148 can have generally ellipsoid shapes and angled side walls 145 (shown in more detail in FIG. 6) that taper inwards from the outer wall of the valve body 140 to the inside of the valve body 148. Such non parallel surfaces can provide for a taper lock connection such as a Luer connector. In some embodiments, the through holes 146, 148 have generally the same shape and configuration. In some embodiments, the through holes 146, 148 have different shapes and configurations.

Figure 5:
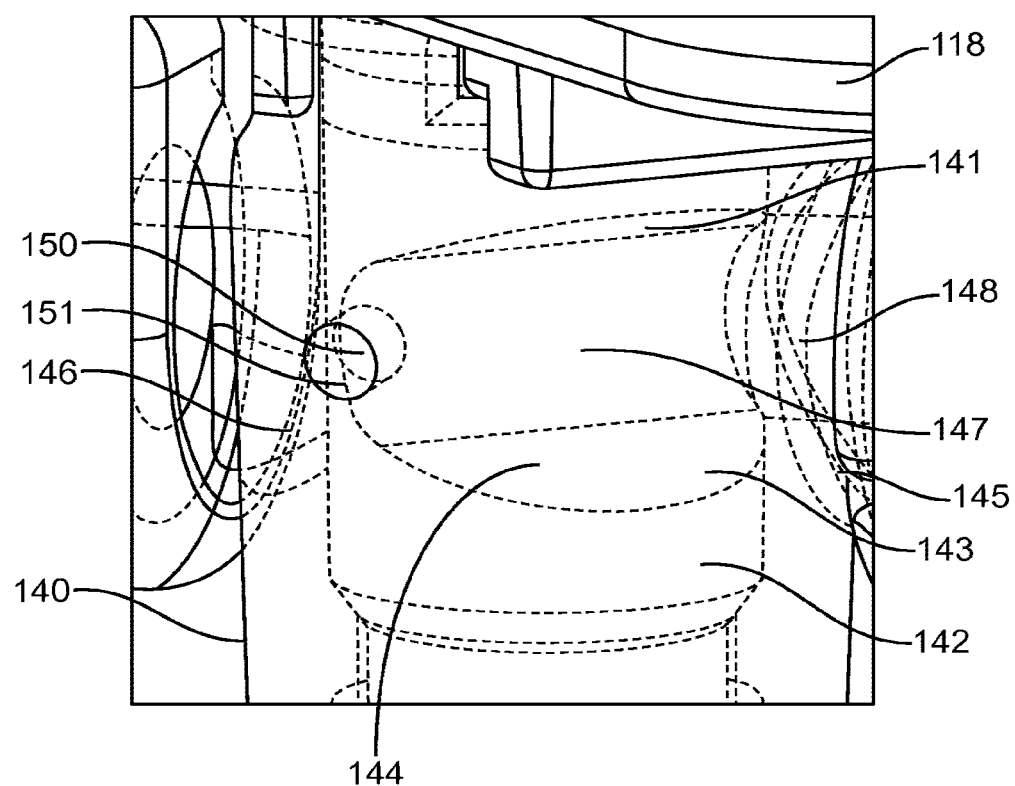
FIG. 5 is an illustration of an embodiment of a valve body.

The valve body 140 comprises a flush hole 150 positioned between the first through hole 146 and the second through hole 148, as shown in FIG. 5. The valve 110 can have three positions: 1.) Closed, in which communication is not allowed between any of the holes 146, 148, 150; 2.) Flush, in which communication is allowed between the second through hole 148 and the flush hole 150; and 3.) Flow, in which communication is allowed between the first through hole 146 and the second through hole 148. In some embodiments, in the flush position, the valve core seals off the first through hole 146, so no flow is allowed to the patient side of the catheter. In some embodiments, in the flow position, no flow is allowed to the flush hole 150. Positioning the flush hole generally orthogonal to the flow path can allow for the flush position to exclude the first through hole 146 and the flow position to exclude the flush hole 150.

The flush hole 150 is shown positioned generally equidistant from through holes 146, 148. In some embodiments, the flush hole can be positioned closer to one of the through holes than the other. The flush hole 150 is shown positioned, in a vertical direction, generally centrally within the flow path. In other embodiments, the flush hole 150 can be positioned higher or lower than the position shown in FIG. 5.

The flush hole 150 is a small hole with a diameter of about 0.050 inches. In some embodiments, the diameter of the flush hole 150 can be about 0.040-about 0.060 inches. The hole size can be selected to optimize flow through the hole 150. The flush hole 150 allows for the flushing of the dead volume within valve 110 and the solution set catheter. In some embodiments, the connector of the solution set catheter (e.g., Baxter UltraBag) may not be UV-transparent. In such embodiments, flushing any residual fluid away from the connector and out of the line can help promote thorough disinfection of the fluid line. The volume of fluid flushed can be selected based on the residual or dead volume within the solution set catheter and the valve. In some embodiments, the dead volume can be as low as about 0.3 cm$^3$. In some embodiments, the dead volume is about 0.3 cm$^3$-1 cm$^3$. In some embodiments, the dead volume is about 0.3 cm$^3$-0.6 cm$^3$ In some embodiments, the dead volume is about 0.3 cm$^3$-2 cm$^3$. In some embodiments, the dead volume is about 1-2 cm$^3$. In some embodiments, the dead volume can be less than or equal to about 2 cm$^3$. In some embodiments, the volume flushed can be about 3 cm$^3$ to allow for about a 1OX margin of safety. Other volumes are also possible. For example, in some embodiments, the volume flushed can be about 1 cm$^3$ to about 5 cm3; about 2 cm$^3$ to about 4 cm$^3$; greater than 5 cm3; etc.

The flush hole 150 can be used to flush fresh dialysate solution to the atmosphere instead of a separate drain container as the flush solution will comprise sterile dialysate. Any microorganisms within the dead volume are already present in the patient environment. As such, the flush solution can be safe to spill to the atmosphere. The flush solution can also be easy to clean after exiting the flush hole as only a small volume of solution is flushed. In some embodiments, the amount of fluid flushed can be caught in something as absorbent and small as a tissue.

The sidewalls 151 of the flush hole 150 can be tapered which can allow for molding. Tapering the walls of the flush hole 150 can also minimize parallel surfaces which are not optimized for UV disinfection as the UV light may be parallel to both surfaces. The wall edges can be sharp or rounded.

Figure 6:
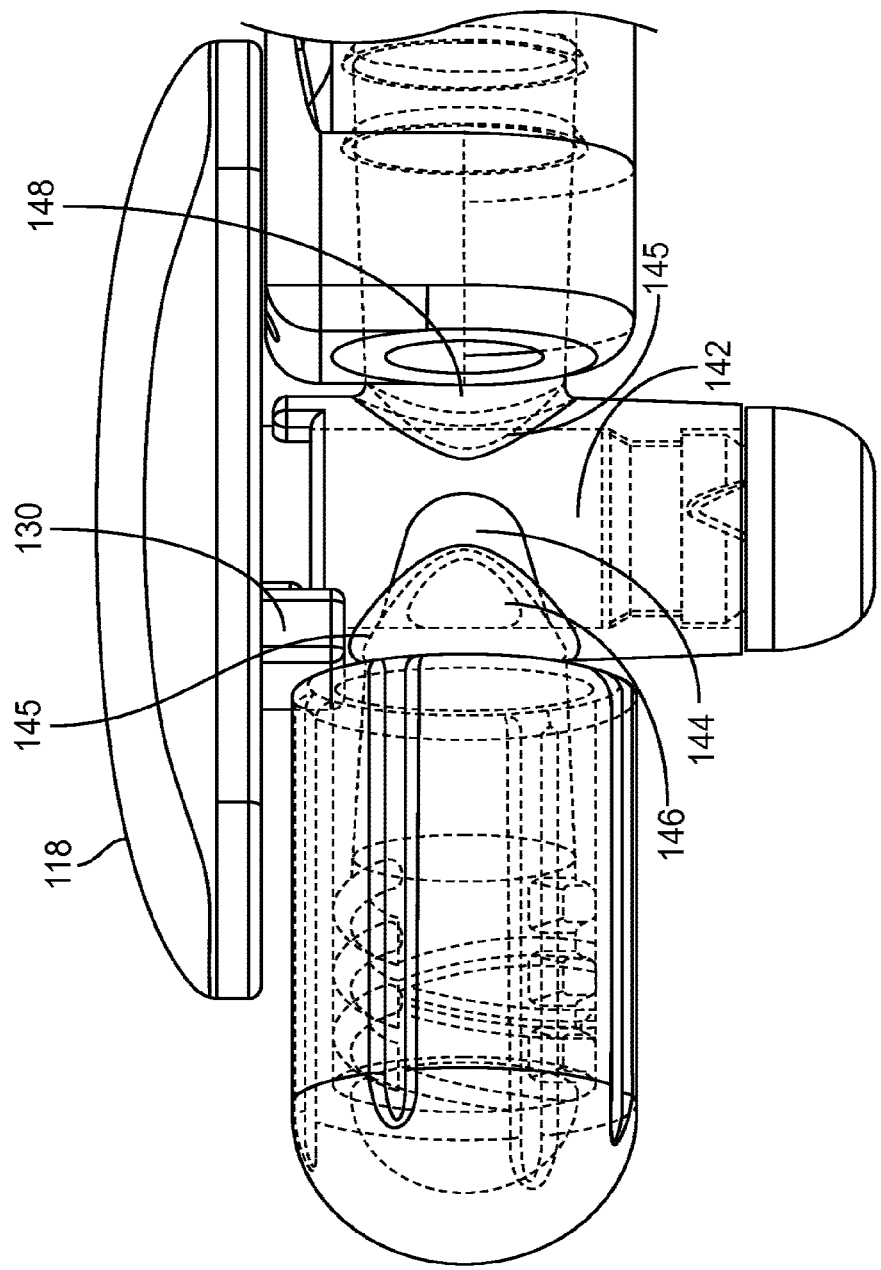
FIG. 6 is an illustration of an embodiment of a valve core.

A valve core 142 is positioned within the valve body. The valve 110 allows fluid flow through the valve via a notch 144 or depression cut out of the valve core 142, as shown in FIGS. 5 and 6. The notch 144 can be generally V-shaped. More particularly, the notch can be shaped as a sideways V when viewing the valve core 142 in a vertical orientation, with the open side of the V on the outer side of the valve core 142. The top surface 141 and the bottom surface 143 of the notch 144 taper towards one another as shown in FIG. 5. The point of the V or innermost surface 147 of the notch 144 can be rounded, as shown in FIGS. 5 and 6. The innermost surface 147 can comprise a circular radius. In some embodiments, the innermost surface 147 can comprise a different radius (e.g., elliptical). In other embodiments, the notch may come to a point. Other shapes are also possible. For example, the notch can be generally hemispherical, partially spherical, cylindrical, parabolic, slit-shaped, etc. Certain notch shapes, like a V-shape, can minimize parallel surfaces within the notch. Minimizing parallel surfaces can enhance UV disinfection effectiveness as parallel surfaces may not receive sufficient UV flux to properly disinfect the area. For example, parallel surfaces may not allow complete disinfection or disinfection in a timely manner. Valves with slits or grooves are known in the art. However, such valves are not optimized for UV disinfection as they have parallel walls not suited for UV disinfection. Because the UV light from external sources may be parallel to the parallel walls, it can be more difficult to ensure that parallel walls have been disinfected.

The valve core 142 can have a diameter of about 0.26 inches. In some embodiments, the diameter of the valve core 142 is about 0.2-0.3 inches.

The notch can be about 0.2 inches tall (direction along the height of the valve core 142). In some embodiments, the notch is about 0.15-0.25 inches tall. The notch can be about 0.2 inches deep (direction into interior of valve core 142). In some embodiments, the notch is about 0.15-0.25 inches deep. The notch can be about 0.26 inches wide (direction across valve core 142). In some embodiments, the notch is about 0.2-0.3 inches wide.

The flush hole 150 can be positioned in the valve body 140 so that it is at the approximate midpoint of the height of the notch 144, as shown in FIG. 5. Positioning the flush hole 150 at this level can help optimize fluid flow during the flush. Positioning the flush hole 150 higher or lower can create more space for accumulation of fluids and contaminants. As such, the flush hole 150 being positioned, in the valve body 140, at the approximate midpoint of the notch 144 can help enhance the effectiveness of the flush.

In one aspect, the height of the notch 144 is about the same as the diameter of one or both of the through holes 146, 148. A circumference of the notch 144 can be the full size of the valve body 140 through holes 146, 148. Matching the size of the notch 144 and through holes 146, 148 can help eliminate choking of the flow and help prevent the through holes 146, 148 and/or notch 144 from getting plugged. A diameter of the through hole can be about 0.131 inches. In some embodiments, the diameter of the through hole is about 0.10-0.16 inches Providing for fluid flow through the valve 110 via a cut-out in the valve core instead of a through-hole in the valve core can allow for exteriorly applied UV light to disinfect the entire valve flow pathway, even if the valve core comprises non-UV transparent material. A valve core with a through-hole would not allow for fluid within a non-UV transmissive core to be disinfected. In some embodiments, the notch 144 has sharp edges, which can leave the maximum amount of surface area for valve core sealing.

Moving to FIG. 7, a bottom view of the transfer valve 110 is shown. As noted above, the valve body 140 and valve core 142 are positioned off-axis with respect to the tubular body 102 and the second connector 112 of the valve 110. A valve core comprising a notch that was centered in the fluid flow can impair the structural integrity of the valve core due to the core being positioned largely within the flow. Additionally, a centered valve core with a notch (vs. flow through) can impede flow more significantly than an off-axis valve core.

Additionally, a notch in the valve core reduces the surface area of the core available for sealing, for a given core diameter. A notch in a centered valve core would more greatly reduce the remaining valve core surface area available for sealing than a notch in an off-axis valve core, assuming the valve body size remains constant. A centered valve core with a notch would require a significantly larger valve body in order to maintain sufficient surface area for sealing various fluid paths. It can be important for the valve core to be able to seal off various flow paths to maintain the sterility of the various components.

An off-axis valve allows more degrees of rotation between the different valve positions. Requiring a user to rotate the valve a greater amount can help a user to select the right valve position. Ease in selecting the proper valve position can reduce user error in operating the valve.

As noted above, the off-axis nature of the valve can help allow for the valve to comprise a minimal volume. Minimizing the volume of the valve can minimize the volume to be disinfected. Minimizing the volume to be disinfected can minimize the amount of contaminants and, thus, the amount of UV required to disinfect. Thus, the UV can be on for less time and/or smaller or fewer bulbs can be used. If less power is required, fewer and/or smaller batteries can be used. Smaller power and/or UV sources can allow the enclosure to be smaller, which can increase comfort and convenience for the patient.

In some embodiments, the valve body 140 and valve core 142 can comprise different materials. For example, the valve core 142 can comprise molded-in seals in lower cost materials, commonly used for valve cores. Such materials can be softer than the UV transparent valve body. In some embodiments, the valve core 142 comprises or is coated with a UV reflective material, which can further optimize incident radiation on any volume to be disinfected.

The valve 110 can comprise a system to show a user the position of the valve. The system can comprise a dome 156 with an indicator positioned at the bottom of the valve core 142. In each valve position (flush, flow, and closed), the dome 156 aligns with symbols 168 on the valve body 140 that indicates the position of the valve 110. The indicator system is described in more detail below.

Figure 8:
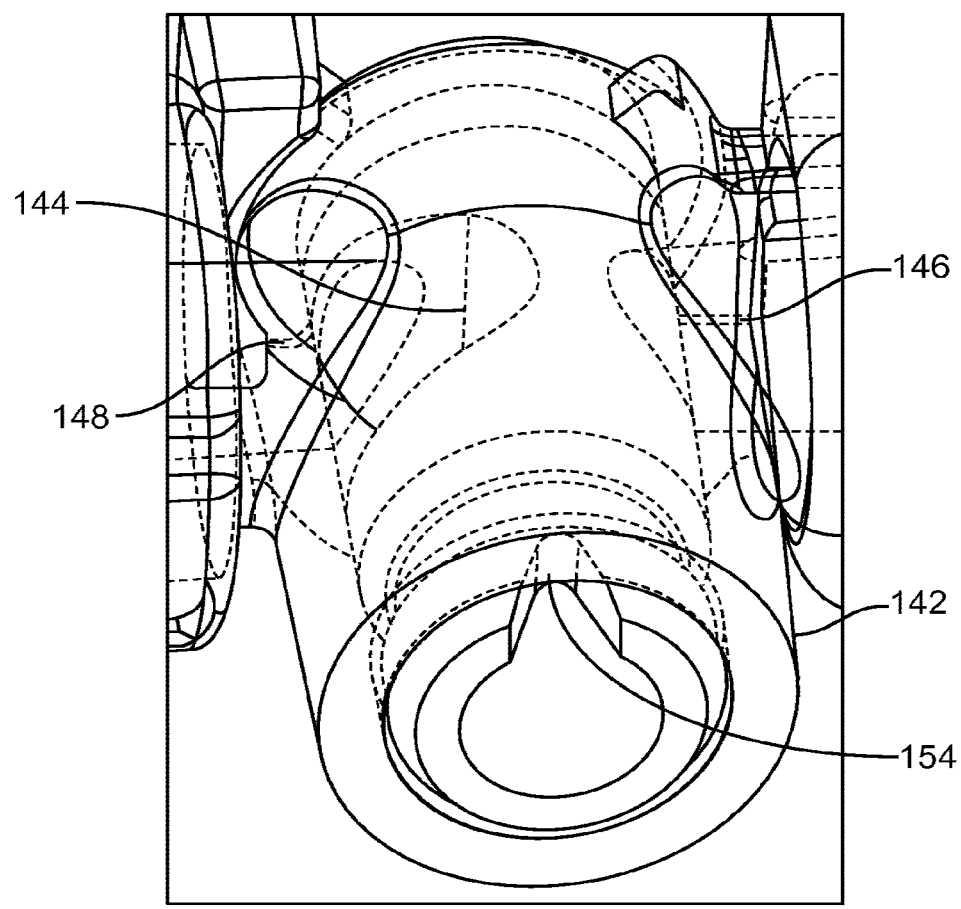
FIG. 8 is an illustration of a valve core key.

The valve 110 can comprise a key 154 positioned on the valve core 142, for example, at the bottom of the valve core as shown in FIG. 8. The key 154 can be used to properly align the dome 156. The key 154 can comprise a feature to receive the dome 156, such as an indentation (e.g., V-shaped indentation, U-shaped indentation, etc.) as shown in FIG. 8. The key 154 can help ensure that the dome 156 does not rotate relative to the valve core 142. Features other than a dome are also possible. For example a square or cylindrical feature can also be used.

As stated above, the dome 156 can be positioned at the bottom of the valve core 142. The dome 156 can help to plug the bottom of the valve core 142, which can help eliminate the accumulation of nooks and crannies, minimizing the amount of contaminants in the valve 110. The dome 156 can have a slightly larger diameter than that of the valve core 142, which can help the dome 156 maintain its position within the core 142. The dome 156 can have a rounded shape, which can provide comfort to the patient while wearing the transfer catheter 100 in between dialysis sessions.

Figure 9A:
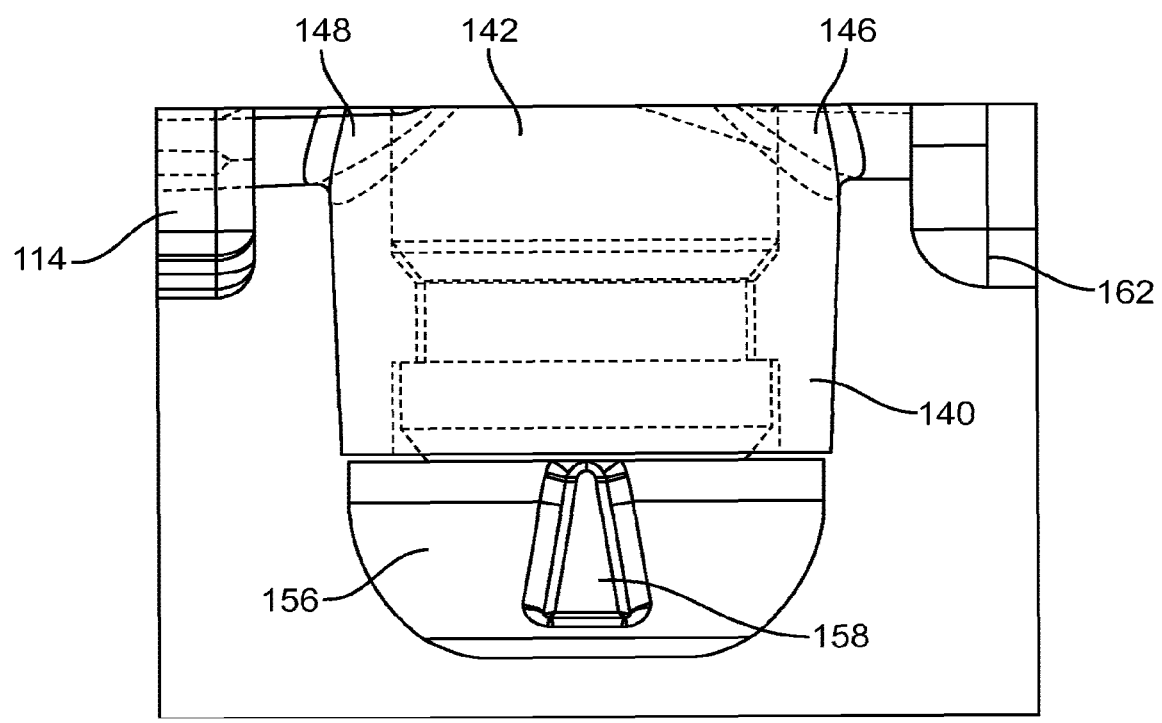
FIGS. 9A and 9B are illustrations of embodiments of a hemispherical dome of a transfer valve.
Figure 9B:
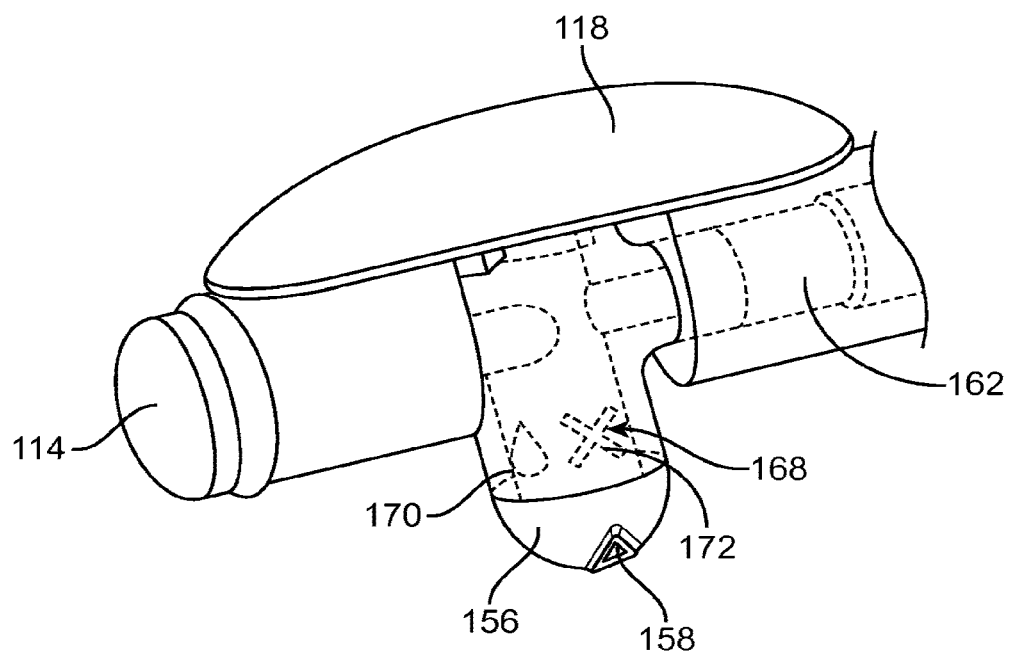

The dome 156 can include an indicator 158, for example, an embossed arrow as shown in FIGS. 9A and 9B. Alignment of the dome indicator 158 and various symbols 168 on the valve body 140 can allow a user to identify the position of the valve 110. As noted above, a center valve position (valve handle 118 in alignment with the tubular body 102) indicates that the valve 110 is in the off or closed position, as shown in FIG. 9B, in which the indicator 158 is aligned with the X symbol or closed icon 172. Turning the valve to the right, or CW, can move the valve 110 into the flush position where indicator 158 can be aligned with the flush icon 170 (water droplet) shown in FIG. 9B. The valve handle 118 can be rotated about 45° to move the valve into the flush position. Turning the valve to the left, or CCW, can move the valve into the flow position. In the flow position, the indicator 158 can be aligned with the flow icon, not shown in FIG. 9B. The flow icon can comprise, for example, a triangle shape. The valve handle 118 can be rotated about 90° to move the valve into the flow position.

Figure 10A:
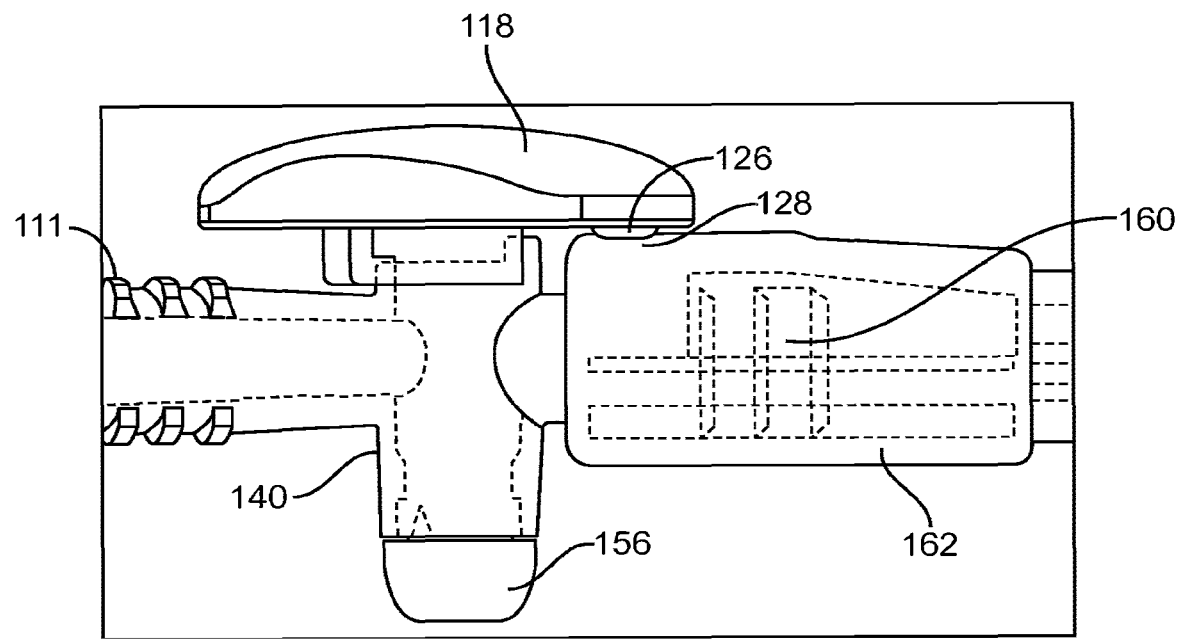
FIGS. 10A and 10B are illustrations of embodiments of a strain relief of a transfer catheter.

The valve 110 can be connected to the tubular body 102 via a connector, such as a barb 160 shown in FIG. 10A. Other connections between the valve 110 and the tubular body 102 are also possible. The connection between the valve 110 and the tubular body 102 can be configured to be fluid-tight in order to keep the interior of the tubular body 102 sterile.

Figure 10B:
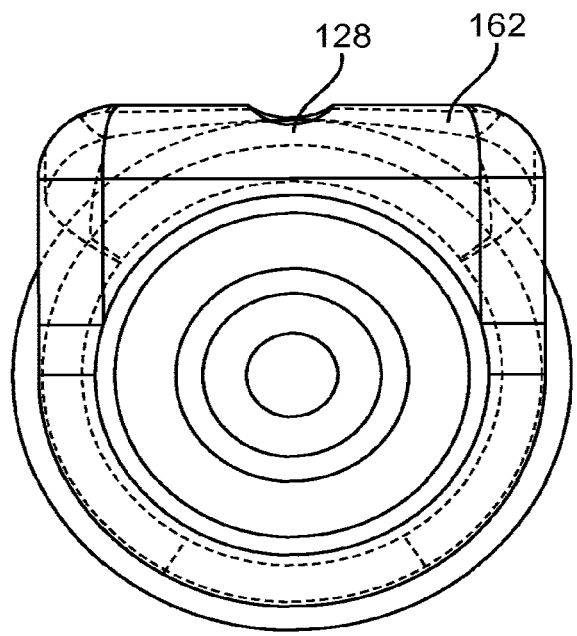

As noted above, the valve handle 118 can include a notch 126 positioned beneath the handle configured to interface with a trough 128, as shown in FIGS. 4G and 10A. The trough 128 can be positioned on the strain relief 162 of the tubular body 102, shown in FIGS. 7, 4G, and 10A. A side view of the strain relief 162 is shown in FIG. 10A. A cross-sectional view of the strain relief 162 taken at a portion of the strain relief beneath the handle 118 is shown in FIG. 10B. The trough 128 can be positioned on a strain relief 162 positioned beneath the front portion of the handle 118 where the valve 110 interfaces with the tubular body 102. The strain relief 162 can comprise an undersized inner diameter which can provide additional grip on the tubular body 102 positioned over the barb 160. The strain relief 162 can be configured to blend into the overall profile of the valve 110. As shown in FIG. 4G, the strain relief 162 can have rounded surfaces 163. The design of the strain relief 162 can allow for the reduction of pinch points, nooks, and crannies. These features of the strain relief 162 can increase comfort for the user.

Figure 11:
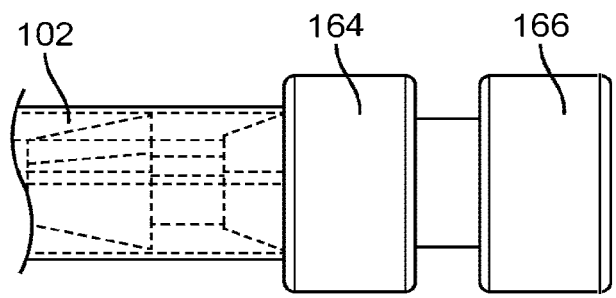
FIG. 11 illustrates an embodiment of a first end of a transfer catheter.

In some embodiments, the tubular body 102, male Luer 164, and cap 166 on the first end 104 of the transfer catheter 100, as shown in FIG. 11, can comprise commercially available components. For example, Qosina parts 11553 and 65702 respectively can be used.

The valve body 140 can include a feature 131 such as a rib, shown in FIG. 4D. The feature 131 can be configured to interact with a groove (not shown) in the strain relief 162 to prevent the strain relief 162 from rotating about the tubular body 102. Rotation prevention can be important as the strain relief 162 is not symmetric, and rotation can change functionality of the catheter 100.

In use, when it is time for a dialysis session, a user begins with the transfer valve 110 in the closed position, as shown in the top view of FIG. 12A. The user may then remove the cap 114 and connect the transfer catheter to a solution set catheter, which comprises a Y-connector to a fresh dialysate bag and a drain bag. Alternatively, separate connections to the dialysate and drain bag can be made. The user can turn the valve 110 about 45° CW to the flush position and flush about 3 cm$^3$ of fresh dialysate out of the flush hole 150. The flush position is shown in a top view in FIG. 12B. After the flush, the user can turn the valve back about 45° CCW to the closed position, shown in the top view of FIG. 12C. The flush can help ensure any dead volume within the valve and beneath the solution set catheter connector, which may not be UV-transmissive, is flushed out of the tubing. The user can then place the connected transfer catheter 100 and solution set catheter so that the connection between them, including the valve is placed within a UV applicator. The UV applicator can be configured to apply UV light from the valve to the connection point between the transfer catheter and the solution set catheter. The UV can be activated to deliver a desired amount of UV light to the catheters. After UV disinfection, the user can turn the valve about 90° CCW to the flow position and begin the drain and fill portion of the dialysis session. The flow position is shown in the top down view of FIG. 12D. After the dialysis session, the user can return the valve 110 to the closed position and re-cap the transfer catheter 100, as shown in FIG. 12A.

U.S. Provisional Patent Application No. 62/052,164, filed Sep. 18, 2014, the entire disclosure of which is hereby incorporated by reference herein, provides examples of UV light applicators. In some embodiments, the UV light applicator can comprise a box comprising a UV light source. The box comprises top and bottom halves hinged together. The box can be rectangular, square, ovular, etc. The box can be configured to be clamped over the connection between the transfer catheter and the solution set catheter. The box can include arcuate sections on each half that form apertures for the catheters when the catheters are positioned within the box. The box can be ambidextrous, meaning the box can be configured to receive the transfer catheter on the right side and the solution set catheter on the left side or vice versa. For example, in some embodiments, the solution set catheter connection may comprise a wide shoulder. The box can be configured to receive the shoulder, via a groove, on either the right or left side of the box.

The box can comprise a curved bottom surface shaped to contour to the thigh of a patient. The box can be sized to receive the transfer catheter disclosed herein. As described above, the transfer catheter can be designed to comprise a small kill zone. As such, the box may only comprise 4 UV lamps and 4 AA batteries as the power source. Such a box can be light enough to rest on the lap of a patient during disinfection or disinfection and dialysis.

Further embodiments of flushing in combination with UV disinfection of a catheter line connection are disclosed in U.S. Provisional Application No. 61/978,556 (the '556

Application), filed on Apr. 11, 2014, entitled CONNECTOR DISINFECTION SYSTEM, the entire disclosure of which is incorporated herein by reference. In the '556 application, embodiments using non-gravity assisted flush are disclosed. For example, a syringe can be used to draw the flush out of PD fluid path. Embodiments disclosed herein relate to a gravity assisted flush, wherein a position of the dialysate bag causes the dialysate to be flushed to the atmosphere through the flush hole. It will be appreciated that any of the features or components of the '556 application can be used in combination with any of the features or components described herein. For example, a syringe or other non-gravity assist can be used to draw the flush out of the valve 110 described herein.

In still further embodiments, the size, shape, and included volume of the valves described herein are selected or optimized to reduce the volume of the valves (e.g., such as the valves described herein and in the '556 application or smaller). Reducing the volume of the valve can reduce the amount of UV used to disinfect and/or reduce the flush volume as the volume of potential contamination is reduced.

As noted above, it is believed that flushing in combination with UV sterilization can provide superior disinfection as compared to UV sterilization alone. PuraCath Medical and Phoenix deVentures performed a study a study comparing the effectiveness of flushing a PD fluid path with dialysate, exposing the path to UV light, or a combination of both. In the study, the inside fluid path of the Y-set connector and transfer catheter were inoculated with *Staphylococcus aureus*. After connecting the transfer catheter to the Y-set, the fluid path was either flushed with dialysate, exposed to UV light, or a combination of both methods.

The study showed a significant reduction in the growth of bacteria in the UV exposure+flush combination group vs. the UV exposure only group. The results indicate that combining a UV light delivery system with flushing, as in the embodiments disclosed herein, may permit a reduction in the risk of peritonitis in PD patients.

It will be appreciated that while the transfer catheter has been described in connection with peritoneal dialysis, the transfer catheter and/or valve can be used in numerous other applications, medical or otherwise such as with Central Venous Catheters (CVC) or Peripherally Inserted Central Catheter (PICC) either of which can be used for dialysis or other interventions.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto. Any feature described in any one embodiment described herein can be combined with any other feature of any of the other embodiment whether preferred or not.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A method for catheter line disinfection, comprising:
    connecting a first catheter to a second catheter using a transfer valve comprising a valve body comprising a first through hole configured to fluidly communicate with the first catheter, a second through hole configured to fluidly communicate with the second catheter, a flush hole positioned between the first through hole and the second through hole, and a generally cylindrical valve core comprising a rounded notch;
    flushing fluid from the second catheter through the flush hole while sealing off fluid communication with the first through hole, said flushing comprising directing fluid flow between the second through hole and the flush hole by way of the rounded notch;
    flowing fluid between the first through hole and the second through hole, by way of the rounded notch, while sealing off fluid communication with the flush hole; and
    removing a cover from the second through hole prior to connecting the second through hole to the second catheter, the cover including a feature that prevents rotation of said cylindrical valve core.

2. The method of claim 1, wherein flushing fluid from the second catheter through the flush hole comprises flushing dead volume within the valve and the second catheter.

3. The method of claim 2, wherein the dead volume is about 0.3 cm$^3$-1 cm$^3$.

4. The method of claim 2, wherein the dead volume is about 0.3 cm$^3$-2 cm$^3$.

5. The method of claim 2, wherein the second catheter is a solution set catheter connected to a drain bag and a dialysate bag.

6. The method of claim 5, wherein flushing fluid from the second catheter through the flush hole comprises flushing dialysate from the dialysate bag to the flush hole.

7. The method of claim 1 further comprising moving the transfer valve from a closed position to a flush position prior to flushing fluid from the second catheter through the flush hole while sealing off fluid communication with the first through hole.

8. The method of claim 1, further comprising moving the transfer valve from a flush position to a flow position prior to flowing fluid between the first through hole and the second through hole while sealing off fluid communication with the flush hole.

9. The method of claim 1, wherein flushing fluid from the second catheter through the flush hole while sealing off fluid communication with the first through hole comprises flushing about 3 cm3 of fluid out of the flush hole.

10. The method of claim 1, further comprising placing the transfer valve in a UV applicator.

11. The method of claim 1, further comprising irradiating the transfer valve with UV light.

12. The method of claim 1, wherein the cover is UV transmissive.

13. The method of claim 1, wherein the valve body and valve core are UV transmissive.

14. The method of claim 1, wherein the valve body is UV transmissive, and the valve core is not.

15. The method of claim 1, wherein the valve body is UV transmissive, and the core comprises a UV reflective coating.

16. The method of claim 1, wherein the rounded notch has only non-parallel surfaces.

17. The method of claim 1, wherein the generally cylindrical valve core is positioned off axis from a flow path between the first through and the second through hole.

18. A method for catheter line disinfection, comprising:
    connecting a first catheter to a second catheter using a transfer valve comprising a UV transparent valve body comprising a first through hole configured to fluidly communicate with the first catheter, a second through hole configured to fluidly communicate with the second catheter, a flush hole positioned between the first through hole and the second through hole, and a generally cylindrical valve core, comprising a rounded notch and a UV reflective surface, operable to rotate in said UV transparent valve body;

flushing fluid from the second catheter through the flush hole while sealing off fluid communication with the first through hole, said flushing comprising directing fluid flow between the second through hole and the flush hole by way of the rounded notch; and flowing fluid between the first through hole and the second through hole, by way of the rounded notch, while sealing off fluid communication with the flush hole.

19. The method of claim 18, further comprising placing the transfer valve in a UV applicator.

20. The method of claim 18, further comprising irradiating the transfer valve with UV light.

21. The method of claim 18, wherein the rounded notch has only non-parallel surfaces.

22. The method of claim 18, wherein the generally cylindrical valve core is positioned off axis from a flow path between the first through and the second through hole.

* * * * *